US012754157B2

(12) United States Patent
Ortega Schulte et al.

(10) Patent No.: US 12,754,157 B2
(45) Date of Patent: Oct. 6, 2026

(54) ELECTROCHEMICAL SENSOR HAVING AN ALKALINE EARTH-MODIFIED ELECTROLYTE FORMULATION

(71) Applicant: HAMILTON AG, Bonaduz (CH)

(72) Inventors: Claudius-Michael Ortega Schulte, Bonaduz (CH); Dirk Schönfuss, Bonaduz (CH)

(73) Assignee: HAMILTON AG, Bonaduz (CH)

( * ) Notice: Subject to any disclaimer, the term of this patent is extended or adjusted under 35 U.S.C. 154(b) by 25 days.

(21) Appl. No.: 18/876,166

(22) PCT Filed: Jul. 6, 2023

(86) PCT No.: PCT/EP2023/068746

§ 371 (c)(1),
(2) Date: Dec. 17, 2024

(87) PCT Pub. No.: WO2024/012989

PCT Pub. Date: Jan. 18, 2024

(65) Prior Publication Data

US 2025/0369914 A1 Dec. 4, 2025

(30) Foreign Application Priority Data

Jul. 12, 2022 (DE) ..................... 10 2022 117 382.8

(51) Int. Cl.

*G01N 27/31* (2006.01)
*G01N 27/30* (2006.01)
*G01N 27/333* (2006.01)
*G01N 33/26* (2006.01)

(52) U.S. Cl.

CPC ........... *G01N 27/31* (2013.01); *G01N 27/301* (2013.01); *G01N 27/333* (2013.01); *G01N 33/26* (2013.01)

(58) Field of Classification Search

CPC .... G01N 27/301; G01N 27/31; G01N 27/333; G01N 33/26

See application file for complete search history.

(56) References Cited

U.S. PATENT DOCUMENTS 11,145,905 B2 10/2021 Vaughey et al.
2006/0006075 A1* 1/2006 O'Neill .................. G01N 27/36 205/787.5
2007/0009689 A1* 1/2007 Murer .................. G01N 27/401 427/372.2

(Continued)

FOREIGN PATENT DOCUMENTS

DE 10354100 A1 6/2005
DE 102018133297 A1 6/2020

(Continued)

OTHER PUBLICATIONS

Patent Cooperation Treaty , International Search Report for PCT/EP2023/068746, 2 pages, dated Oct. 26, 2023.

*Primary Examiner* — C. Sun

(74) *Attorney, Agent, or Firm* — Viksnins Harris Padys Malen LLP

(57) ABSTRACT

The invention relates to an electrochemical sensor having a porous diaphragm and an electrolyte formulation that comprises at least one solvent, at least one electrolyte from the group of alkali metal salts and at least one alkaline earth metal ion, and to an electrolyte formulation.

21 Claims, 3 Drawing Sheets

Diffusion potential with respect to NaCl (16 mS/cm)

(56) References Cited

U.S. PATENT DOCUMENTS

| | | | | |
|---|---|---|---|---|
| 2008/0149482 | A1* | 6/2008 | Marett | G01N 27/301 204/414 |
| 2013/0161191 | A1* | 6/2013 | Wilhelm | G01N 27/31 29/25.03 |
| 2014/0034515 | A1 | 2/2014 | Thrier | |
| 2020/0057017 | A1 | 2/2020 | Zhang et al. | |

FOREIGN PATENT DOCUMENTS

| | | | |
|---|---|---|---|
| EP | 1219959 | A1 | 7/2002 |
| EP | 1636149 | B1 | 9/2007 |

* cited by examiner

ELECTROCHEMICAL SENSOR HAVING AN ALKALINE EARTH-MODIFIED ELECTROLYTE FORMULATION

CROSS-REFERENCE TO RELATED APPLICATION(S)

This patent application claims the benefit of priority of German application Serial No. 102022117382.8, filed Jul. 12, 2022, which application is herein incorporated by reference.

The invention relates to an electrochemical sensor having a reference electrode having a porous diaphragm and an electrolyte formulation comprising at least one alkaline earth metal ion, and to an electrolyte formulation for an electrochemical sensor.

Electrochemical sensors are used to analyze media, especially liquid process media, in order to determine certain properties of the corresponding medium, in particular the pH, the redox potential, and/or the presence of certain ions or types of molecules in the medium. The medium to be investigated is also referred to synonymously as a measuring fluid or working fluid.

The properties that can be determined using electrochemical sensors are summarized below under the term "electrochemical measurement variable". In order to determine electrochemical measurement variables, in each case suitable measuring electrodes are used which have the property that when the measuring electrode contacts the medium to be investigated, either an electrochemical potential is established which depends on the electrochemical measurement variable to be determined, for example the pH or the concentration of a certain type of ion. This potential is recorded as a measuring signal, which is why such sensors are also called potentiometric sensors.

Alternatively, in so-called amperometric sensors, a certain potential difference (voltage) is applied between a measuring electrode and a reference electrode in such a way that the types of ions or molecules to be measured are oxidized or reduced at the measuring electrode. The current flowing in this case between the measuring electrode and a third electrode, specifically the so-called counter electrode, is measured. Said current is proportional to the concentration of the types of ions or molecules to be determined. Both potentiometric and amperometric electrochemical sensors thus require a reference half-cell or reference electrode.

Electrochemical sensors are often designed as combination electrodes, the spaces of the reference half-cell and the measuring electrode being arranged concentrically. A combination electrode is understood to be a combination of a measuring electrode and a reference electrode that are housed in a single rod. The term working electrode is also used synonymously with the term measuring electrode, and the term comparison electrode is also used synonymously with the term reference electrode.

The measuring electrode can be designed as an ion-selective electrode which comes into direct contact with the medium to be investigated so that the ion-selective electrode and the medium directly form a system whose electrochemical potential depends on the concentration of a certain type of ion in the medium.

In the case of sensors with a glass membrane, however, the measuring electrode itself already comprises a system consisting of a measuring lead electrode in contact with an internal electrolyte, the internal electrolyte then being in contact with the medium to be investigated via the glass membrane. For example, in the case of pH electrodes, a potential difference across the glass membrane that is located between the medium and the internal electrolyte of the measuring electrode, that depends on the pH of the medium, is usually measured. The internal electrolyte then forms a buffer system and is selected in such a way that an electrical potential difference across the glass membrane is established that is as proportional as possible to the desired electrochemical measurement variable.

In general, a system with a measuring electrode and possibly associated internal electrolyte/measuring membrane is referred to below as a measuring half-cell of an electrochemical sensor, the measuring electrode being provided in a measuring half-cell space in which the internal electrolyte is also located.

In the case of potentiometric or amperometric sensors, the measuring electrode generally consists of a metal such as platinum, gold, iridium, rhodium or other metals, metal alloys or metal oxides such as $IrO_2$, $RuO_2$, $TiO_2$, $TaO_2$, $ZnO_2$ or others.

Another type of electrochemical sensors are so-called ISFET (ion selective field effect transistor) sensors, in which an ion-sensitive layer is applied to the gate touching the medium, which layer creates a potential depending on the concentration of the species to be determined, which potential regulates the current flow between the source and drain of a field effect transistor.

Because electrical potentials can only ever be recorded or adjusted as a difference with respect to a reference potential, an electrochemical sensor always requires a measuring electrode and a further reference electrode that provides an electrochemical reference potential as a reference value for the measuring signal supplied by the measuring electrode.

The reference electrode comprises a redox system consisting of a reference electrode in contact with a reference electrolyte. The reference redox system is selected so that when the reference electrode contacts the reference electrolyte, a known, very stable and easily reproducible electrochemical potential is established. Generally, any reference redox system of the type described is referred to below as a reference half-cell of an electrochemical sensor.

The reference half-cell comprises a reference half-cell space in which the reference electrode and the reference electrolyte are located. The electrochemical potential of the reference half-cell should change as little as possible due to the contact of the reference electrolyte with the medium to be investigated.

Common reference half-cells are based on electrodes of the second type in which a metal reference lead electrode coated with a poorly soluble metal salt is in contact with a reference electrolyte that contains a chemically inert salt readily soluble in the reference electrolyte with the same anion as that of the poorly soluble electrode coating. The reference electrolyte is often a liquid or a rather viscous gel, in particular an aqueous salt solution or an aqueous gel of a particular salt.

A common redox system used for reference electrodes, as may also be intended for use with the present invention, consists of an Ag wire with a coating of AgCl (silver-silver chloride electrode) which is immersed in a reference electrolyte of aqueous KCl solution.

Other redox systems that are also suitable for use with the present invention are also based on the use of KCl, such as the calomel redox system ($Hg/Hg_2Cl_2$).

The reference electrolyte is also selected based on the fact that it has good electrical conductivity, is chemically inert, and its ions have as equal a mobility as possible.

In the case of potentiometric sensors such as pH sensors, the reference half-cell and measuring half-cell must be brought into electrolytic contact with the medium to be investigated in order to determine the respective electrochemical measurement variable. A voltage difference is then determined which corresponds to the difference between the electrochemical potentials of the reference half-cell and the measuring half-cell.

The electrochemical potential arising in each case between the measuring half-cell and the medium to be investigated, as well as between the reference electrode and the reference electrolyte, depends on many factors. Therefore, when starting up an electrochemical sensor, it is necessary to first calibrate it with solutions or electrolytes of known ion activity (standardized buffer solutions are usually used for this purpose) before the desired electrochemical measurement variable can be quantitatively determined from the voltage difference determined for an unknown medium.

In order to establish an electrolytic contact between the reference electrolyte and the medium to be investigated which is necessary for the measurement, the reference half-cell is in contact with its environment via an opening, a diaphragm or a similar connection.

The diaphragm is characterized by the fact that it prevents an intermixing of the KCl solution and the medium to be investigated, but allows for a charge transport between the KCl solution and the medium in the form of an ion migration. Diaphragms with a porous structure are often used for this purpose. An interfering factor of the diaphragm is its diffusion potential. This potential always occurs at the phase boundary between two electrolytes of different concentration or composition. The diffusion potential is due to the different migration velocities of the ions through the diaphragm based on the interaction of the ions with the diaphragm surface, which in turn depend on the charge and size of the ion type, i.e. on the charge density and extent of its hydration shell and the diaphragm material.

With increasing differences in the ion concentration between the medium and the reference electrolyte, the diffusion gradients and thus also the diffusion potentials increase.

If anions diffuse faster than cations or vice versa, a potential arises at the boundary between the two solutions. In order to keep the diffusion potential at the diaphragm of a reference electrode as small as possible, the different ions in the reference electrolyte should have the same ion mobility. In the case of a 3 M KCl solution, this ideal state is almost achieved. In general, it can be stated that the higher the flow rate of the reference electrolyte through the diaphragm, the smaller the diffusion potential.

However, this is counteracted by the desire for a slow exit of the reference electrolyte and the ions from the reference electrolyte space in order to delay the loss of the reference electrolyte through outflow and a depletion of the reference electrolyte in ions as long as possible, and thus increase the service life and potential stability of the sensor. This is achieved by adding thickeners and/or uncharged organic compounds to the reference electrolyte, which in turn results in lower KCl concentrations.

EP 1 219 959 A1 describes an electrochemical sensor for detecting a pH which, in addition to a measuring electrode, has two reference electrodes that have different potential stability. The reference electrode with the higher potential stability is used to determine the measured value in the measuring medium, while the reference electrode with the lower potential stability serves to determine the salt concentration in the reference electrolyte. Porous or fine-pored materials are described here as suitable for diaphragms, in particular porous ceramic plugs, ground glass, cotton fibers, synthetic fibers, metal threads, porous plastics plugs and wooden pins.

EP 1 636 149 B1 describes an electrochemical sensor with a diaphragm that has an open porosity between 20 and 38%. The material of the diaphragm, namely a porous ceramic, is impregnated with a lyo-gel precursor material during its production which then changes into a lyo-gel. By at least partially filling the cavities of the porous ceramic with lyo-gel, the result is a porous ceramic with smaller pores. However, the reduced pores cause the diffusion potentials to be particularly large, especially in the case of a medium to be investigated having a low ion concentration.

The objective is to provide an electrochemical sensor with an improved reference half-cell.

This objective is achieved by an electrochemical sensor according to claim 1 and an electrolyte solution according to claim 21. Further advantageous embodiments and designs of the invention are apparent from the de-pendent claims, the figures and the embodiment examples. The embodiments of the invention can be combined with one another in an advantageous manner.

A first aspect of the invention relates to an electrochemical sensor for measuring a working fluid, having a reference electrode arranged in a first volume having a first electrically conductive fluid, and at least one working electrode, wherein the first volume is delimited at least by a porous diaphragm with an open porosity of less than 35%, and wherein the first electrically conductive fluid is an electrolyte formulation which comprises at least one solvent, at least one electrolyte from the group of alkali metal salts and at least one alkaline earth metal ion in a concentration in the range of 20 to 95 mmol/kg.

The first electrically conductive fluid can also be referred to as the reference electrolyte.

It has been surprisingly shown that $ZrO_2$-based diaphragms have a high adsorptive affinity to alkaline earth ions so that the presence of this type of ion in the reference electrolyte in the concentration range of 20-95 mmol/kg impressively damps the diffusion potentials. The alkaline earth metal ion doping in the reference electrolyte advantageously guarantees a permanent and stationary concentration of diffusion potential-damping cations at the diaphragm location of an electrochemical sensor. This reduces measurement errors of the corresponding sensors caused by diffusion potentials.

The open porosity of the diaphragm is determined by mercury porosimetry. Common diaphragms have a porosity of 35% or more. In contrast, the diaphragm of the sensor according to the invention has an open porosity of less than 35%. Preferably, the diaphragm has an open porosity of less than 30%, more preferably less than 25%, and particularly preferably in the range of 18-22%. The reduction in the open porosity of the diaphragm inter alia has the advantage that it extends the duration of possible dry storage of the sensor, which is limited, inter alia, by the continuous outflow of the reference electrolyte from the diaphragm. However, the reduction in the open porosity of the diaphragm influences the diffusion potentials at the diaphragm that occur when the sensor is used, especially with working fluids with a low conductivity, so that this measure would have to limit the operational field of application or the specification of the sensor, especially in the case of diluted solutions as working fluids.

The combination according to the invention of reducing the open porosity with the use of at least one alkaline earth metal ion in the reference electrolyte solution produces a synergistic effect since both enable an extension of the specification of the sensor. For example, the operational field of application of the sensor can be extended to solutions (working fluids) with lower ion concentrations down to 0.5 mS/cm. Although the lower porosity of the diaphragm increases the diffusion potential, the alkaline earth metal ions in the reference electrolyte dampen the diffusion potential. As already described, the lower porosity of the diaphragm reduces the outflow of ions from the diaphragm. This also extends the service life and dry storage time of the sensor. It is also possible to reduce the volume of the reference electrolyte and to make the sensors smaller without sacrificing performance comparable to conventional sensors.

As the open porosity values decrease, the permeability of the diaphragm becomes increasingly lower. Preferably, the diaphragm therefore has an open porosity of at least 5%, more preferably of at least 10%. Thus, the diaphragm preferably has an open porosity of at least 5% and less than 35%, more preferably of at least 5% and less than 30%, more preferably of at least 5% and less than 25%. Alternatively, the diaphragm preferably has an open porosity of at least 10% and less than 35%, more preferably of at least 10% and less than 30%, more preferably of at least 10% and less than 25%. As already described, the diaphragm particularly preferably has an open porosity in the range of 18-22%.

Preferably, the alkaline earth metal ion is a magnesium ion. Also preferably, the alkaline earth metal ion is a calcium ion. Said alkaline earth metal ions can also both be present. Further alkaline earth metal ions can also be present in the electrolyte solution.

Preferably, the concentration of the alkaline earth metal ion in the electrolyte formulation is in the range of 30-85 mmol/kg. More preferably, the concentration of the alkaline earth metal ion in the electrolyte formulation is in the range of 40-75 mmol/kg, and particularly preferably 55 mmol/kg.

In a further preferred embodiment, the concentration of the alkaline earth metal ion in the electrolyte formulation is in the range of 20-50 mmol/kg.

Preferably, the alkaline earth metal ion is present in the electrolyte solution as part of an inorganic salt of the alkaline earth metal. Preferably, the inorganic salt of the alkaline earth metal is a chloride salt. It is preferably magnesium chloride and/or calcium chloride or their hydrates.

The electrolyte formulation comprises at least one, in particular exactly one, electrolyte from the group of alkali metal salts. Preferably the electrolyte is potassium chloride. Potassium chloride is easy to provide because it is often used in a reference electrolyte solution. The damping effect according to the invention by alkaline earth metal ions, in conjunction with the reduced diaphragm porosity according to the invention, is particularly suitable for solutions containing potassium chloride since a lower loss of potassium (potassium outflow) from the sensor into the working fluid enables the sensor to be used in fermenters and stirred incubators or culture vessels for the cultivation of cells. For example, mammalian cells do not respond well to excessive potassium. This can be particularly important in small culture volumes due to potassium outflow from the sensor. The sensor according to the invention advantageously has a low potassium footprint and is thus particularly suitable for use in mammalian cell cultures. This is particularly important in the biotechnological pharmaceutical industry. Furthermore, a comparatively lower chloride loss (chloride outflow) from the sensor leads to lower drift (i.e. increased drift stability) of the reference electrode and to higher measurement quality during the operational service life of the sensor.

In a preferred embodiment, the electrolyte formulation comprises potassium chloride and magnesium chloride. In a further preferred embodiment, the electrolyte formulation comprises potassium chloride and calcium chloride.

The solvent in the electrolyte formulation is in particular water. Preferably, the electrolyte formulation has a water content of at least 20 wt %.

Preferably, the electrolyte formulation comprises at least one evaporation-inhibiting agent and/or at least one thickening agent. The evaporation-inhibiting agent is, for example, glycerol. The thickening agent is, for example, xanthan.

The diaphragm of the sensor according to the invention is preferably aceramic diaphragm. The ceramic diaphragm can, for example, comprise a porous ceramic made of porcelain, alumina, spinel, forsterite and/or zirconium dioxide (also called zirconia). The use of these ceramics as diaphragms is known. Zirconium dioxide can have calcium oxide, magnesium oxide or yttrium oxide as a stabilizing additive.

Preferably, the ceramic diaphragm has yttrium oxide-doped zirconium dioxide. Particularly preferably, the yttrium oxide doping is 8 mol %. Zirconium dioxide with an yttrium oxide doping of 8 mol % is particularly suitable for glass electrodes due to its hardness, its expansion coefficient and corrosion resistance. The stabilizing effect of yttrium oxide in the zirconium dioxide structure is based on the increased formation of cubic crystal phases, compared to the thermodynamically more unstable tetrahedral and monoclinic material phases. Other stabilizing oxide components that promote the formation of crystalline cubic phases are calcium oxide and magnesium oxide.

Preferably, the sensor is a potentiometric sensor that is selected from the group consisting of a pH sensor, redox sensor and ion-selective sensor. The reference half-cell can, however, also be used for other electrochemical sensors such as amperometric or ISFET sensors.

The sensor is preferably a combination electrode. Advantageously, combination electrodes can be used in particular as pH sensors.

A second aspect of the invention relates to an electrolyte formulation for an electrochemical sensor with a porous diaphragm, comprising at least one solvent, at least one electrolyte from the group of alkali metal salts, and at least one alkaline earth metal ion in a concentration in the range of 20-95 mmol/kg.

The advantages of the electrolyte formulation according to the invention correspond to the advantages of the electrochemical sensor according to the invention.

The invention is explained in more detail with reference to the figures, in which.

Figure 1:
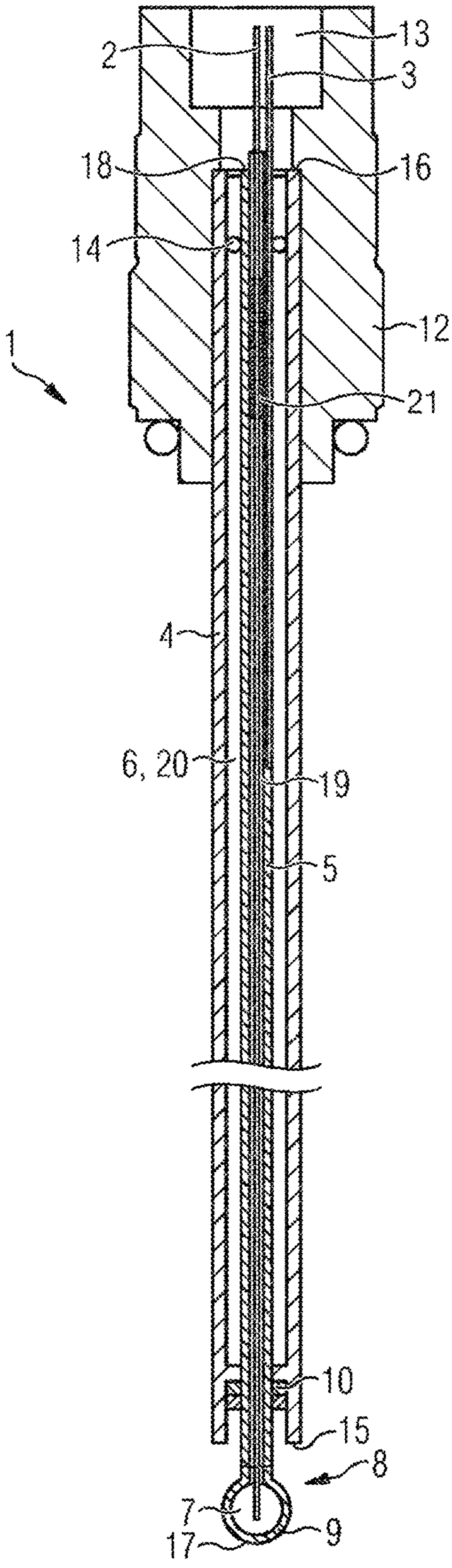
FIG. 1 is a schematic representation of a longitudinal section through a combination electrode according to an embodiment of the invention.

For measuring a working fluid, a combination electrode 1 according to the representation in FIG. 1 has a working electrode 2, a reference electrode 3, a diaphragm 10 and a first electrically conductive fluid 6. The first electrically conductive fluid 6 is in contact with the reference electrode 3 and the diaphragm 10 such that the diaphragm 10 is connected to the reference electrode 3 in an electrically conductive manner via the first electrically conductive fluid 6. The first electrically conductive fluid 6 is also referred to as the reference electrolyte.

The combination electrode 1 can be a pH combination electrode and/or a redox sensor. The pH combination electrode can be a pH glass electrode.

The combination electrode 1 has an outer tube 4 and an inner tube 5 which is arranged within the outer tube 4. The outer tube 4 is also synonymously referred to here as external tube, and the inner tube 5 is also synonymously referred to here as internal tube.

The volume between the two tubes is configured as a reference space in which the first electrically conductive fluid 6 is arranged. The outer tube 4 has a first outer tube longitudinal end 15 and a second outer tube longitudinal end 16. A first inner tube longitudinal end 17 is arranged in the region of the first outer tube longitudinal end 15. A second inner tube longitudinal end 18 is arranged in the region of the second outer tube longitudinal end 16.

In the inner tube 5, an inner tube space 19 is formed in which a second electrically conductive fluid 7 (also referred to as inner electrolyte) is arranged. In addition, the inner tube 5 according to FIG. 1 has a storage vessel 8 at its first longitudinal end 17, the volume of which is fluidically connected to the inner tube space 19 and has a larger diameter than the inner tube 5 so that a larger amount of the second electrically conductive fluid 7 can be provided.

The combination electrode 1 has an opening of the reference space 20 in the form of an annular gap in the region of the first outer tube longitudinal end 15 and first inner tube longitudinal end 17. The diaphragm 10 is arranged in the opening and seals the opening. In this case, the thickness of the diaphragm 10 is specified in relation to the extension between the first inner tube longitudinal end 17 and the second inner tube longitudinal end 18. The thickness of the diaphragm 10 can range from 0.1 mm to 1.0 mm, in particular from 0.35 mm to 0.7 mm. A fluid channel (not shown) can be provided from the diaphragm, which leads to the first outer tube longitudinal end 15.

The diaphragm 10 is characterized by the fact that it prevents an intermixing of the first electrically conductive fluid 6 and the working fluid, but allows for a charge transport between the first electrically conductive fluid 6 and the working fluid. In order to carry out a measurement in an operation of the combination electrode 1, the side of the diaphragm 10 facing away from the first electrically conductive fluid 6 must be contacted with the working fluid. In addition, the combination electrode 1 has a glass membrane 9 in the region of the first inner tube longitudinal end 17. The glass membrane 9 is electrically conductively connected to the working electrode 2 via the second electrically conductive fluid 7. The first electrically conductive fluid 6 and the second electrically conductive fluid 7 are electrically isolated from one another. In order to measure the working fluid, the working fluid is also contacted with the side of the glass membrane 9 facing away from the second electrically conductive fluid 7, and an electrical voltage is measured between the working electrode 2 and the reference electrode 3.

The diaphragm 10 comprises, as a material, zirconium dioxide with an yttrium oxide doping of 8 mol %. Other porous ceramic materials can also be used.

Figure 2:
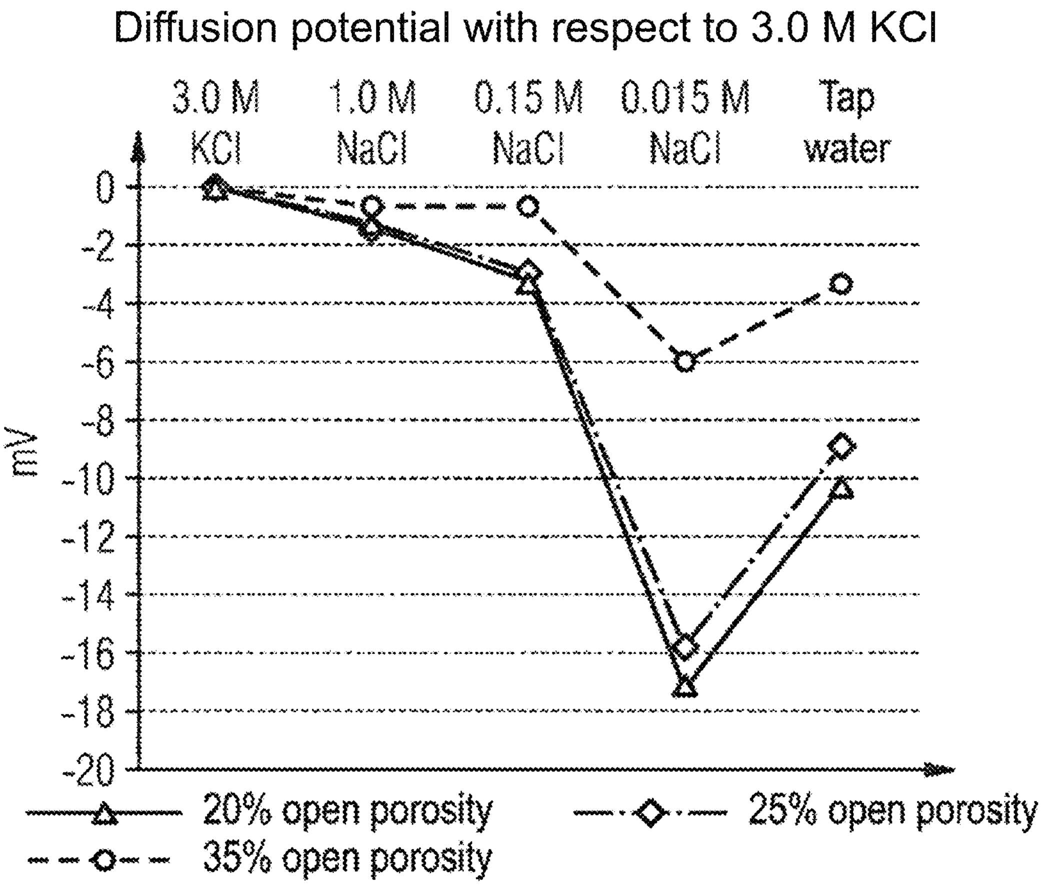
FIG. 2 is a graph of the interrelationship between diaphragm porosity and diffusion potential.

The material of the diaphragm 10 has an open porosity of 20%. The porosity of the diaphragm 10 can limit the diffusion of ions from the first electrically conductive fluid 6, however, this increases the diffusion potential. The interrelationship between porosity and diffusion potential at different salinities is shown in FIG. 2. The dashed line corresponds to an open porosity of 35%, the solid line marked with diamonds to an open porosity of 25%, and the solid line marked with triangles to an open porosity of 20%. The damping effect of tap water compared to 0.015 M NaCl is also clear. Control measurements have surprisingly shown that this damping effect can be attributed to traces of calcium ions in the tap water.

The first electrically conductive fluid 6 has a composition that contains a calcium and/or magnesium ion in a certain concentration. By way of example, various compositions according to the invention are shown in Table 1 as formulation 0, 1, 2, 3 and 4. In this case, the values are given in grams unless otherwise stated in the table.

| Ingredient | Form. 0 | Form. 1 | Form. 2 | Form. 3 | Form. 4 |
|---|---|---|---|---|---|
| Xanthan | 16.7 | 16.7 | 17.2 | 16.7 | 16.7 |
| Glycerol | 303.9 | 303.9 | 313.46 | 303.9 | 303.9 |
| $MgCl_2$ | 0 | 2.0 | 4.1 | 0 | 8.0 |
| $CaCl_2$ | 0 | 0 | 0 | 8.9 | 0 |
| KCl | 117.3 | 117.3 | 121.0 | 117.3 | 117.3 |
| $H_2O$ | 562.1 | 517.5 | 533.8 | 517.5 | 560 |
| Alkaline earth (mmol/kg) | 0.0 | 22.0 | 44.1 | 83.9 | 84.0 |

Figure 3:
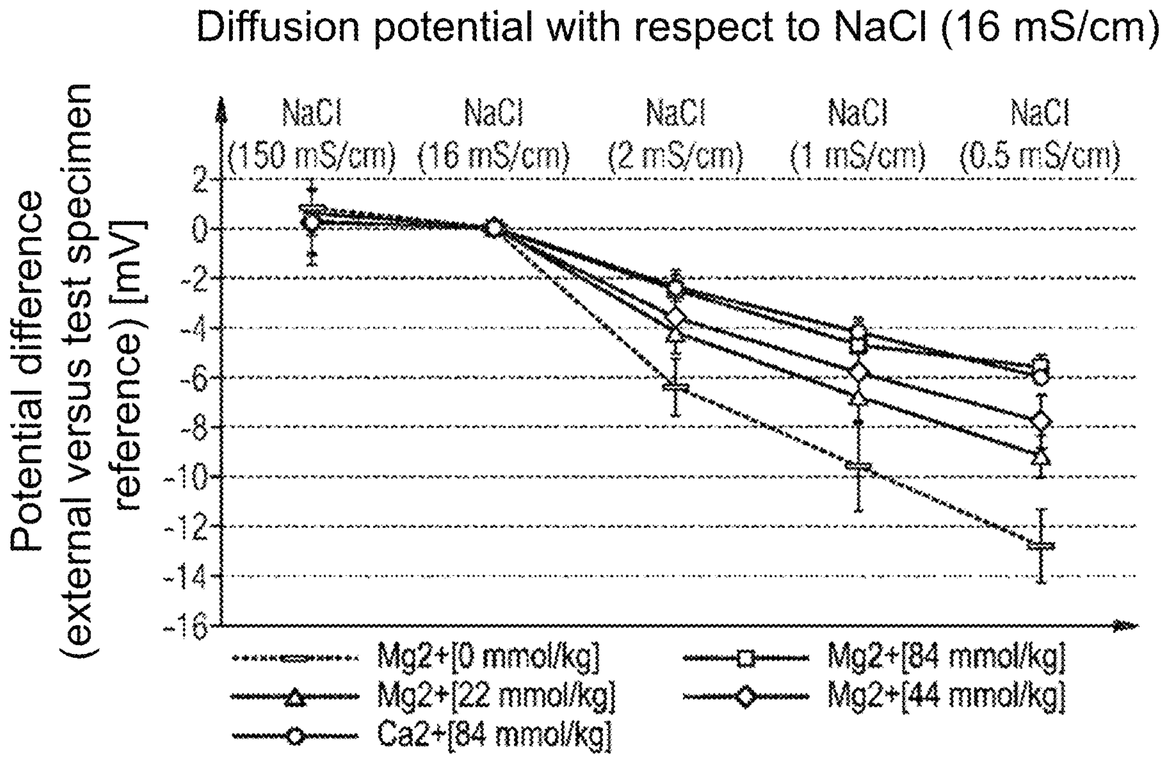
FIG. 3 is a graph of the dampening effect of alkaline earth metal ions on the diffusion potential.

Another example of the damping effect of alkaline earth metal ions can be found in FIG. 3. Here, the potential difference is shown versus the diffusion potential with respect to sodium chloride as an electrolyte contact solution (first electrically conductive fluid 6). The diffusion potential measurement was carried out by potentiometric differential measurement using a Protos® transmit-ter from Knick Elektronisch Messgeräte GmbH & Co KG. The potentiometric measurements are carried out by comparing two local measurement positions. The first local measurement position is called the external reference and consists of a glass shaft half electrode system made of Ag/AgCl/KCl and a 35% pore diaphragm system (i.e. a diaphragm with an open porosity of 35%) made of fully stabilized zirconia ceramic, with a 3 M KCl solution as electrode filling (Hamilton standard reference electrode); the second local measurement position, called the test specimen reference electrode, is also a glass shaft half electrode system consisting of Ag/AgCl/KCl, a thickened salt-electrolyte mixture and a diaphragm made of a porosity-reduced fully stabilized zirconia ceramic. Both glass shaft half-electrode systems are electrolytically kept connected ionically via an aqueous contact solution with different conductivity, and the measurement is carried out at a constant agitation of 100 rpm. With increasing dilution of the electrolyte contact solutions, the potential difference between the two local measurement positions increases due to diffusion, as a result of which a deviation of the reference potential measurement stability is determined. The diffusion is substantially regulated by the diaphragm porosity, viscosity and codiffusion processes of the formulated salt-electrolyte mixture.

The graph also clearly shows here that, compared to a solution without alkaline earth metal ion (dashed line), there is a damping effect on the diffusion potential when magnesium ions are present (solid line with triangles: 22 mmol/kg), and this effect increases with increasing concentration (solid line with diamonds: 44 mmol/kg, solid line with squares: 84 mmol/kg). In addition, a damping effect of calcium ions is also shown (solid line with circles: 84 mmol/kg). The values in FIG. 3 are given as rounded values.

LIST OF REFERENCE SIGNS

1 combination electrode
2 working electrode
3 reference electrode
4 outer tube
5 inner tube
6 first electrically conductive fluid
7 second electrically conductive fluid
8 storage vessel
9 glass membrane
10 diaphragm
12 head part
13 casting compound
14 sealing ring
15 first outer tube longitudinal end
16 second outer tube longitudinal end
17 first inner tube longitudinal end
18 second inner tube longitudinal end
19 inner tube space
20 reference space

The invention claimed is:

1. An electrochemical sensor for measuring a working fluid, having a reference electrode (3) arranged in a first volume having a first electrically conductive fluid (6), and at least one working electrode (2), wherein the first volume is delimited at least by a porous diaphragm (10) with an open porosity of less than 35%, and wherein the first electrically conductive fluid (6) is an electrolyte formulation which comprises at least one solvent, at least one electrolyte from the group of alkali metal salts and at least one alkaline earth metal ion in a concentration in the range of 20 to 95 mmol/kg.

2. The sensor according to claim 1, wherein the diaphragm (10) has an open porosity of less than 30%.

3. The sensor according to claim 1, wherein the diaphragm (10) has an open porosity of less than 25%.

4. The sensor according to claim 1, wherein the diaphragm (10) has an open porosity in the range of 18-22%.

5. The sensor according to claim 1, wherein the alkaline earth metal ion is a magnesium ion.

6. The sensor according to claim 1, wherein the alkaline earth metal ion is a calcium ion.

7. The sensor according to claim 1, wherein the concentration of the alkaline earth metal ion in the electrolyte formulation is in the range of 30-85 mmol/kg.

8. The sensor according to claim 7, wherein the concentration of the alkaline earth metal ion is in the range of 40-75 mmol/kg.

9. The sensor according to claim 8, wherein the concentration of the alkaline earth metal ion is 55 mmol/kg.

10. The sensor according to claim 1, wherein the concentration of the alkaline earth metal ion is in the range of 20-50 mmol/kg.

11. The sensor according to claim 1, wherein the alkaline earth metal ion is present as part of an inorganic salt of the alkaline earth metal.

12. The sensor according to claim 11, wherein the inorganic salt of the alkaline earth metal is a chloride salt.

13. The sensor according to claim 1, wherein the electrolyte of the electrolyte formulation is potassium chloride.

14. The sensor according to claim 1, wherein the electrolyte formulation has a water content of at least 20 wt %.

15. The sensor according to claim 1, wherein the electrolyte formulation comprises at least one evaporation-inhibiting agent and/or at least one thickening agent.

16. The sensor according to claim 1, wherein the diaphragm (10) is a ceramic diaphragm.

17. The sensor according to claim 16, wherein the ceramic diaphragm comprises yttrium oxide-doped zirconium dioxide.

18. The sensor according to claim 17, wherein the yttrium oxide doping is 8 mol %.

19. The sensor according to claim 1, wherein the sensor is a potentiometric sensor selected from the group consisting of a pH sensor, redox sensor and ion-selective sensor.

20. The sensor according to claim 1, wherein the sensor is a combination electrode.

21. An electrolyte formulation for an electrochemical sensor with a porous diaphragm, comprising at least one solvent, at least one electrolyte from the group of alkali metal salts and at least one alkaline earth metal ion in a concentration in the range of 20-95 mmol/kg.

* * * * *